United States Patent
Cho et al.

(10) Patent No.: US 12,076,709 B2
(45) Date of Patent: Sep. 3, 2024

(54) METHOD FOR PRODUCING A CATALYST FOR OXIDATIVE DEHYDROGENATION OF BUTENE

(71) Applicant: LG CHEM, LTD., Seoul (KR)

(72) Inventors: Ara Cho, Daejeon (KR); Young Chang Byun, Daejeon (KR); Gyo Hyun Hwang, Daejeon (KR); Jungup Bang, Daejeon (KR); Cheolock Song, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 18/134,487

(22) Filed: Apr. 13, 2023

(65) Prior Publication Data

US 2023/0271169 A1    Aug. 31, 2023

Related U.S. Application Data (62) Division of application No. 16/756,561, filed as application No. PCT/KR2018/014726 on Nov. 27, 2018, now Pat. No. 11,648,536.

(30) Foreign Application Priority Data

Nov. 28, 2017   (KR) ........................ 10-2017-0160634

(51) Int. Cl.
| | | |
|---|---|---|
| *B01J 23/887* | (2006.01) | |
| *B01J 35/40* | (2024.01) | |
| *B01J 37/00* | (2006.01) | |
| *B01J 37/03* | (2006.01) | |

(Continued)

(52) U.S. Cl.
CPC .......... *B01J 23/8876* (2013.01); *B01J 35/40* (2024.01); *B01J 37/0036* (2013.01); *B01J 37/009* (2013.01); *B01J 37/03* (2013.01); *C07C 5/48* (2013.01); *C07C 11/167* (2013.01)

(58) Field of Classification Search
None
See application file for complete search history.

(56) References Cited

U.S. PATENT DOCUMENTS

| | | |
|---|---|---|
| 3,932,551 A | 1/1976 | Grasselli et al. |
| 4,212,766 A | 7/1980 | Brazdil et al. |
| 7,482,500 B2 | 1/2009 | Johann et al. |

(Continued)

FOREIGN PATENT DOCUMENTS

| | | |
|---|---|---|
| CN | 104549338 A | 4/2015 |
| CN | 106881098 A | 6/2017 |

(Continued)

OTHER PUBLICATIONS

U.S. Appl. No. 16/756,561, filed Apr. 16, 2020.

(Continued)

*Primary Examiner* — Coris Fung
*Assistant Examiner* — Keling Zhang
(74) *Attorney, Agent, or Firm* — BRYAN CAVE LEIGHTON PAISNER LLP (57) ABSTRACT

A catalyst for oxidative dehydrogenation of butene and a method for producing the same are described. The method includes forming a first coprecipitate, forming a second coprecipitate, and mixing the first and second coprecipitates under conditions that product a catalyst having a favorable surface chemistry profile.

3 Claims, 1 Drawing Sheet

(51) Int. Cl.
*C07C 5/48* (2006.01)
*C07C 11/167* (2006.01)

(56) References Cited

U.S. PATENT DOCUMENTS

| | | |
|---|---|---|
| 2008/0233045 A1 | 9/2008 | Ozkan et al. |
| 2011/0004041 A1 | 1/2011 | Chung et al. |
| 2013/0281748 A1 | 10/2013 | Cha et al. |
| 2015/0126774 A1 | 5/2015 | Hiraoka et al. |
| 2016/0368839 A1 | 12/2016 | Hwang et al. |
| 2018/0208685 A1 | 7/2018 | Okumura et al. |

FOREIGN PATENT DOCUMENTS

| | | | | |
|---|---|---|---|---|
| GB | 2023597 A | * | 1/1980 | .......... B01J 23/8877 |
| JP | 5513187 A | | 1/1980 | |
| JP | 2011-115681 A | | 6/2011 | |
| JP | 2013-43125 A | | 3/2013 | |
| JP | 2014-520067 A | | 8/2014 | |
| KR | 10-2009-0103424 A | | 10/2009 | |
| KR | 10-2011-0078040 A | | 7/2011 | |
| KR | 10-2012-0073733 A | | 7/2012 | |
| KR | 10-2014-0131861 A | | 11/2014 | |
| KR | 10-2015-0141879 A | | 12/2015 | |
| KR | 10-2016-0061144 A | | 5/2016 | |
| WO | 2013161703 A1 | | 10/2013 | |
| WO | 2017047710 A1 | | 3/2017 | |

OTHER PUBLICATIONS

Moro-Oka et al., "Multicomponent Bismuth Molybdate Catalyst: A Highly Functionalized Catalyst System for the Selective Oxidation of Olefin", Advances in Catalysis 40 (1994), 233-273.

Jung et al., "Catalytic Performance of Co9Fe3Bi1Mo12O51 Catalysts in the Oxidative Dehydrogenation of n-Butene to 1,3-Butadiene: Effect of pH in the Preparation of Co9Fe3Bi1Mo12O51 Catalysts by a Co-precipitation Method", Catalysis Letters, 2009, vol. 129, pp. 228-232.

Arora et al., "Surface Aspects of Bismuth-Metal Oxide Catalysts", Journal of Catalysis, vol. 159, No. 1, pp. 1-13.

Jiang et al., "The Effect of Micro-Morphology of Bi2O3 on Catalytic Properties of Co/Bi Catalyst for Wet Air Oxidation of Acetic Acid", React. Kinet. Catal. Lett., vol. 82, No. 1, pp. 49-56.

Arora et al., Surface aspects of bismuth-metal oxide catalysts, Journal of Catalysis, 159, 1-13, 1996 (Year: 1996).

Jiang et al., The effect of micro-morphology of Bi2O3 on catalytic properties of Co/Bi catalyst for wet air oxidation of acetic acid, React. Kinet. Catal. Lett., 82, 1, 49-56, 2004 (Year: 2004).

Introduction to Transition metals II, https://chem.libretexts.org/Bookshelves/Inorganic_Chemistry/Supplemental_Modules_and_Websites_(Inorganic_Chemistry)/Descriptive_Chemistry/Elements_Organized_by_Block/3d-Block_Elements/1b_Properties_of_Transition_Metals/Introduction_to_Transition_Metals_II) (Year: 2020).

Machine Translation of KR 20160061144 A (Year: 2016).

* cited by examiner

METHOD FOR PRODUCING A CATALYST FOR OXIDATIVE DEHYDROGENATION OF BUTENE

The present application is a Divisional Application of U.S. patent application Ser. No. 16/756,561 filed on Apr. 16, 2020, which is a National Phase entry pursuant to 35 U.S.C. § 371 of International Application Serial No. PCT/KR2018/014726 filed on Nov. 27, 2018, and claims priority to and the benefit of the filing date of Korean Patent Application No. 10-2017-0160634 filed with Korean Intellectual Property Office on Nov. 28, 2017, the entire contents of which are incorporated herein by reference.

FIELD

The present invention relates to a catalyst for oxidative dehydrogenation of butene and a method for producing the same.

BACKGROUND 1,3-Butadiene, a colorless and odorless flammable gas, is a material that is easily liquefied when the pressure is applied and is easily flammable. It is a very important basic material used as a raw material of various petrochemical products, for example, synthetic rubbers such as styrene-butadiene rubber (SBR), polybutadiene rubber (BR), and acrylonitrile-butadiene-styrene rubber (ABS).

As methods of preparing 1,3-butadiene, there are broadly naphtha cracking, direct dehydrogenation of butene, or oxidative dehydrogenation of butene.

Among the above methods, the naphtha cracking is responsible for 90% or more of 1,3-butadiene supplied to the market, and it is performed in such a manner that 1,3-butadiene is selectively extracted from a base oil which is produced from a cracker in a steam cracking process for the production of ethylene.

However, since the main purpose of the steam cracking process is for the production of base oils other than 1,3-butadiene, such as ethylene, so it is not effective for producing 1,3-butadiene and a lot of energy consumption may be required due to a high reaction temperature.

Therefore, dehydrogenation has received attention in which 1,3-butadiene is obtained by removing hydrogen from butene in a C4 mixture which remains after extracting all of the useful basic oils in the steam cracking process.

The dehydrogenation of butene includes a direct dehydrogenation reaction and an oxidative dehydrogenation reaction. In this case, the above reactions can be used for the production of n-butene (normal butene, 1-butene) or (cis, trans)-2-butene.

Since the direct dehydrogenation of butene is a reaction in which 1,3-butadiene is obtained by removing hydrogen from butene, and a highly endothermic reaction, it is thermodynamically disadvantageous. Therefore, a high-temperature reaction condition is required, and even if the conversion rate is increased by increasing the temperature, there is a problem that a side reaction is increased in accordance with the temperature rise, and thus the yield of 1,3-butadiene is decreased.

Since the oxidative dehydrogenation of butene is a reaction in which n-butene and oxygen are reacted to produce 1,3-butadiene and water, and an exothermic reaction different from the direct dehydrogenation, it is thermodynamically very advantageous. Therefore, it may obtain 1,3-butadiene with a high yield even at a relatively low reaction temperature as compared with the direct dehydrogenation.

Current known catalysts used for the oxidative dehydrogenation of butene include a ferrite-based catalyst, a tin-based catalyst, a bismuth-molybdenum-based catalyst, and the like.

Among the above catalysts, the bismuth-molybdenum-based catalyst including a bismuth-molybdenum catalyst composed only of bismuth and molybdenum metal oxides and a multicomponent bismuth-molybdenum catalyst in which various metal components are added on the basis of bismuth and molybdenum.

The multicomponent bismuth-molybdenum catalyst is produced by co-precipitation of a nitrate precursor of various metals including bismuth and an aqueous ammonium molybdate solution. However, when a multicomponent bismuth-molybdenum catalyst having a complicated composition is prepared by a general co-precipitation method, it is difficult to efficiently form a catalytically active phase.

Therefore, there is a need for a method for efficiently synthesizing a catalyst for oxidative dehydrogenation of butene capable of exhibiting high catalytic activity under relatively low temperature reaction conditions.

SUMMARY

An object of the present invention is to provide a catalyst for oxidative dehydrogenation of butene capable of exhibiting high catalytic activity under relatively low temperature reaction conditions.

Another object of the present invention is intended to provide a method for producing the above-mentioned catalyst for oxidative dehydrogenation of butene.

In one aspect of the invention, there is provided a catalyst for oxidative dehydrogenation of butene, which is represented by the following Composition Formula 1,
wherein a surface composition of the catalyst measured by XPS (X-ray photoelectron spectroscopy), a molar content of bismuth (Bi) is higher than the molar content of cobalt (Co), $$Mo_a Bi_b Co_c (M1)_d (M4)_e O_f \qquad \text{[Composition Formula 1]}$$

in Composition Formula 1, Mo is molybdenum, Bi is bismuth, Co is cobalt, O is oxygen, M1 is one or more Group 1 metal elements, M4 is one or more period 4 transition metal elements excluding cobalt (Co), a is from 9 to 25, b is from 0.5 to 2, c is from 1 to 10, d is from 0.01 to 1, e is from 0.5 to 5, f is from 30 to 50.

In another aspect of the invention, there is provided a method for producing a catalyst for oxidative dehydrogenation of butene comprising:

producing a first coprecipitate by mixing an aqueous solution containing a cobalt salt and a period 4 transition metal salt excluding cobalt, and an aqueous solution of ammonium molybdate, and performing co-precipitation;

producing a second coprecipitate by mixing an aqueous solution of bismuth (Bi) salt and ammonium molybdate and performing co-precipitation;

mixing the first coprecipitate and the second coprecipitate;

wherein producing the first coprecipitate or producing the second coprecipitate is independently performed by further mixing an aqueous solution containing a Group 1 metal salt.

The catalyst for oxidative dehydrogenation of butene according to the present invention has a relatively large amount of Mo—Bi phase acting as a reaction active phase on the surface, and therefore, can exhibit high catalytic activity, high conversion rate and high butadiene selectivity even in relatively low temperature conditions in the oxidative dehydrogenation reaction of butene.

DETAILED DESCRIPTION

The terms "first," "second," etc. may be used herein to describe various elements, and these terms are only used to distinguish one element from another.

The technical terms used herein is for the purpose of describing exemplary embodiments only and is not intended to limit the scope of the invention. The singular forms "a," "an" and "the" are intended to include plural forms, unless the context clearly indicates otherwise. It should be understood that the terms "comprise," "include", "have", etc. are used herein to specify the presence of stated features, integers, steps, components or combinations thereof, but do not preclude the presence or addition of one or more other features, integers, steps, components, or combinations thereof.

Since a variety of modifications may be made to the present invention and there may be various forms of the invention, specific examples are illustrated and will be described in detail below. However, it should be understood that these are not intended to limit the present invention to the specific disclosure, and that the present invention includes all the modifications, equivalents or replacements thereof without departing from the spirit and technical scope of the invention.

As used herein, the oxidative dehydrogenation of butene means a reaction that can be represented by the following Reaction Scheme, and the butene used in the reaction means both 1-butene, cis, and trans-2-butene.

[Reaction Scheme]

Hereinafter, embodiments of the present invention will be described in detail.

According to one embodiment of the invention, there is provided a catalyst for oxidative dehydrogenation of butene, which is represented by the following Composition Formula 1, wherein, based on an analysis of the surface composition of the catalyst measured by XPS (X-ray photoelectron spectroscopy), the molar content (atomic ratio, %) of bismuth (Bi) is higher than the molar content of cobalt (Co).

$$Mo_aBi_bCo_c(M1)_d(M4)_eO_f \quad \text{[Composition Formula 1]}$$

in Composition Formula 1, Mo is molybdenum, Bi is bismuth, Co is cobalt, O is oxygen, M1 is one or more Group 1 metal elements, M4 is one or more period 4 transition metal elements excluding cobalt (Co), a is from 9 to 25, b is from 0.5 to 2, c is from 1 to 10, d is from 0.01 to 1, e is from 0.5 to 5, f is from 30 to 50, which is a value determined by the valence of the other metal.

According to the results of studies conducted by the present inventors, even if the total composition in a bismuth-molybdenum based catalyst is similar, significant differences in catalytic activity can be exhibited depending on the type of metal added, the production method and the production condition.

Thus, the catalyst for oxidative dehydrogenation of butene according to one embodiment of the invention is represented by the following Composition Formula 1, and when the surface of the catalyst is measured by XPS, the molar ratio of bismuth (Bi): cobalt (Co) has a larger value than that of the catalyst produced by a conventional general co-precipitation method.

$$Mo_aBi_bCo_c(M1)_d(M4)_eO_f \quad \text{[Composition Formula 1]}$$

in Composition Formula 1, Mo is molybdenum, Bi is bismuth, Co is cobalt, O is oxygen, M1 is one or more Group 1 metal elements, M4 is one or more period 4 transition metal elements excluding cobalt (Co), a is from 9 to 25, b is from 0.5 to 2, c is from 1 to 10, d is from 0.01 to 1, e is from 0.5 to 5, f is from 30 to 50, which is a value determined by the valence of the other metal.

At this time, the period 4 transition metal means a metal element excluding cobalt among metal elements in the fourth period of the periodic table, and specific examples thereof include at least one selected from the group consisting of titanium, vanadium, chromium, manganese, iron, nickel, copper, and zinc. Preferably, one or more of iron, manganese, and copper may be used.

A Group 1 metal means an alkali metal element of the periodic table, and specific examples thereof include at least one selected from the group consisting of sodium, potassium, rubidium, and cesium. Preferably, potassium and/or cesium may be used.

In this case, when the Group 1 metal includes two types of metal elements, or when the period 4 transition metal includes two types of metal elements, the Composition Formula 1 described above can be represented by the following Composition Formulas 1-1 to 1-3, respectively.

$$Mo_aBi_bCo_c(M1)_d(M41_{e1}M42_{e2})O_f \quad \text{[Composition Formula 1-1]}$$

$$Mo_aBi_bCo_c(M11_{d1}(M12_{d2})(M4)_eO_f \quad \text{[Composition Formula 1-2]}$$

$$Mo_aBi_bCo_c(M11_{d1}(M12_{d2}(M41_{e1}M42_{e2})O_f \quad \text{[Composition Formula 1]}$$

in Composition Formula 1-1 to 1-3, Mo is molybdenum, Bi is bismuth, Co is cobalt, O is oxygen, M1 is a Group 1 metal element, M11 and M12 are Group 1 metal elements different from each other, M4 is a period 4 transition metal element excluding cobalt (Co), M41 and M42 are the period 4 transition metal elements different from each other excluding cobalt (Co), a is from 9 to 25, b is from 0.5 to 2, c is from 1 to 10, d is from 0.01 to 1, e is from 0.5 to 5, d1 and d2 are each independently 0.01 to 0.99, e1 and e2 are each independently 0.5 to 4.5, and f is from 30 to 50, which is a value determined by the valence of the other metal.

The bismuth-molybdenum-based multicomponent metal oxide catalyst is known to be effective for oxidative dehydrogenation of butene. Although there are various opinions on the effect of α-, β-, γ-phases of bismuth-molybdenum on the catalyst for partial oxidation reaction, it is generally known that the oxygen mobility of bismuth-molybdenum affects the oxidative dehydrogenation of butene, similarly to the Mars-van Krevelen reaction mechanism.

The oxygen diffusion rate and the reaction activity in these catalysts differ depending on the crystal phase and it has been reported to be the highest in γ-phase. In addition, when α-phase and γ-phase, and β-phase and γ-phase are present together, it has been reported that excellent activity and selectivity are visible due to a synergetic effect.

There are two major reasons why the multicomponent bismuth-molybdenum catalyst is superior in activity relative to a single bismuth-molybdenum. The first is an increase in surface area, and the second is related to the oxidation reaction mechanism. In the partial oxidation reaction of propylene, the activation of oxygen and the reaction of propylene take place at different active sites, and the activated oxygen atom is known to be "bulk diffusion" to active sites which are on Bi—Mo—O phase through Co—Fe—Mo—O phase. This type of oxygen transfer can occur in catalytic systems containing bivalent and trivalent metal cations, especially $Fe^{3+}$, which can form a lattice vacancy. In such system, active oxygen is smoothly supplied, thereby increasing the activity of the catalyst and increasing the number of reaction active phases.

Therefore, in order to enhance the reaction activity and the selectivity, it is necessary to produce a catalyst having a structure capable of effectively reacting the oxygen active site and the reaction active site. The structure of the bismuth-molybdenum-based multicomponent metal oxide catalyst is greatly affected not only by the composition and the original consumption of each component but also by the production method and the production conditions.

In the catalyst of the present invention, the bismuth-molybdenum phase serving as the reaction active site and the cobalt-molybdenum phase serving to activate oxygen and to supply oxygen to the active sites are respectively coprecipitated and mixed, thereby containing a relatively large amount of a bismuth-molybdenum phase on the surface of the catalyst. Due to such a unique composition, high catalytic activity can be realized.

According to one embodiment of the present invention, the catalyst for oxidative dehydrogenation of butene may preferably satisfy the following Calculation Formula 1.

BARS/BART>6　　　　　　　　　　[Calculation Formula 1]

in Calculation Formula 1,

BARS is the molar content (atomic ratio, %) of bismuth/ the molar content (atomic ratio, %) of cobalt on the catalyst surface, measured by XPS, and BART is the molar content (atomic ratio, %) of bismuth/ the molar content (atomic ratio, %) of cobalt in the entire catalyst, measured by ICP-OES.

That is, the catalyst according to one embodiment of the present invention takes a form which includes bismuth in a relatively high amount on the surface, specifically in a relative content of about 6 times or more, or about 6 to about 20 times, as compared to the entire catalyst composition. As a result, it is possible to realize higher reaction activity and butadiene selectivity compared to conventional bismuth-molybdenum-based catalysts.

Further, according to Calculation Formula above, the catalyst of the present invention can contain a relatively large amount of cobalt in the part excluding the surface (oxygen active part), and thus, make smooth supply of oxygen to the reaction active part as the reaction proceeds and promote regeneration of bismuth-molybdenum-oxygen crystal structure, thereby significantly increasing the activity of the overall reaction.

Meanwhile, the catalyst for oxidative dehydrogenation of butene described above can be produced by a method including the steps of:

A) a first co-precipitation step of producing a first coprecipitate by mixing an aqueous solution containing a cobalt salt and a period 4 transition metal salt excluding cobalt, and an aqueous solution of ammonium molybdate, and performing co-precipitation;

B) a second co-precipitation step of producing a second coprecipitate by mixing an aqueous solution of bismuth (Bi) salt and ammonium molybdate and performing co-precipitation;

C) a step of mixing the first coprecipitate and the second coprecipitate;

wherein the first co-precipitation step or the second co-precipitation step is independently performed by further mixing an aqueous solution containing a Group 1 metal salt.

According to the production method of one embodiment of the present invention, the catalyst can be produced with high reproducibility by a two-step co-precipitation method in which the precursor compounds are different from each other. In addition, the reaction active part where partial oxidation reaction takes place and the oxygen active part where oxygen activation takes place are respectively coprecipitated, so that each active part is efficiently synthesized. In particular, it is possible to produce a catalyst having a relatively high content of bismuth on the surface than a conventional catalyst, and thus, it becomes possible to produce a catalyst capable of realizing high activity and butadiene selectivity as described above.

According to one embodiment of the invention, the first and second co-precipitation steps can each independently proceed under stirring at a temperature of about 30 to about 50° C. for about 0.5 to about 2 hours, and thus can easily proceed under relatively mild conditions.

At this time, the period 4 transition metal means a metal element excluding cobalt among the metal elements in the fourth period of the periodic table, and specific examples thereof include at least one selected from the group consisting of titanium, vanadium, chromium, manganese, iron, nickel, copper, and zinc. Preferably, one or more of iron, manganese and copper can be used.

In this case, the Group 1 metal means an alkali metal element of the periodic table, and specific examples thereof include at least one selected from the group consisting of sodium, potassium, rubidium, and cesium. Preferably, potassium and/or cesium may be used.

A multicomponent bismuth-molybdenum catalyst can be produced by the above-described method. In addition to the above-mentioned bismuth, cobalt and molybdenum, each metal element may be included together as a catalyst component, thereby serving to enhance the stability of the catalyst according to the change of the oxidation number of the active metal in the catalyst.

In this case, the metal salt mentioned above refers to a nitrate, a hydroxide, a chloride salt, and the like. In view of the solubility and reactivity during the preparation of aqueous solutions, it may be preferable to use a nitrate and/or a chloride salt.

Then, after the step of mixing the first coprecipitate and the second coprecipitate, the method may further include drying, grinding and classification.

The drying step is a step of removing the solvent from the slurry made by mixing the first and second coprecipitates, thereby obtaining a catalytically active component, and can proceed at about 100° C. to about 150° C. for about 1 to about 48 hours.

In addition, the grinding and classification steps can adjust the size of the catalyst particles to increase the surface area of the reactive site in the oxidative dehydrogenation of butene and enhance the reaction activity.

Specifically, in the classification step, after the grinding, particles having a size of about 355 μm or less can be collected and used as a catalyst.

The catalyst particles obtained as above may be used after being molded into a certain shape according to oxidative dehydrogenation reaction conditions of butene, such as a reactor. Subsequently, the method may further include firing.

The firing may be performed by a heat treatment at about 400° C. to about 600° C. in an air atmosphere.

Meanwhile, the catalyst according to one embodiment of the invention can be used for an oxidative dehydrogenation of butene.

The butene used as the raw material may be one that is contained in the C4 mixture produced as a by-product in the naphtha cracking process. The C4 mixture contains about 30% by weight or more of 1-butene, and about 25% by weight or more of butanes including isobutane, and also contains other impurities such as isobutene.

The reaction temperature of the oxidative dehydrogenation of butene is preferably maintained within the range of about 250° C. to about 450° C., or about 350° C. to 420° C., in order to optimize the activation of the catalyst.

In addition, the reaction pressure is from about 0 atm to about 10 atm. If the reaction pressure is out of the above range, the selectivity of 1,3-butadiene may be reduced.

During the reaction, supplying butene and oxygen, which are reactants, together with nitrogen and steam may be preferable in terms of reaction efficiency and temperature control, and the ratio may be determined according to a method generally used in the art.

Hereinafter, the function and effect of the present invention will be described in more detail by way of specific examples of the invention. However, these examples are presented for illustrative purposes only, and are not intended to limit the scope of the invention.

EXAMPLES

Production of Catalyst

Example 1 (Corresponding to Sample 1)

Precursor aqueous solution A: 0.2 g of $KNO_3$, 11.7 g of $CsNO_3$, 63.4 g of $Fe(NO_3)_3 \cdot 9H_2O$ and 281.2 g of $Co(NO_3)_2 \cdot 6H_2O$ were sequentially charged into a beaker containing 183 g of distilled water, and then dissolved with stirring.

Precursor aqueous solution B: 58.6 g of $Bi(NO_3)_3 \cdot 5H_2O$ was added to a beaker containing 100 g of distilled water, and 14 g of nitric acid was added with stirring.

Precursor solution C: 245.2 g of $(NH_4)_6Mo_7O_{24} \cdot 4H_2O$ was added to a beaker containing 900 g of distilled water, and dissolved with stirring.

Precursor aqueous solution C': 10.7 g of $(NH_4)_6Mo_7O_{24} \cdot 4H_2O$ was added to a beaker containing 180 g of distilled water, and dissolved with stirring.

The precursor aqueous solution A was added to the precursor aqueous solution C (40° C.) under stirring using a dropping funnel and allowed to precipitate (first coprecipitate). Dropping was carried out for about 1 hour, and then the precipitate was stirred under the same conditions for about 30 minutes.

At the same time, the precursor aqueous solution B was added to the precursor aqueous solution C' (40° C.) under stirring using a dropping funnel (second coprecipitate). Dropping was carried out for about 30 minutes and then the mixture was stirred under the same conditions for about 1 hour.

The second coprecipitate was subjected to aging and was added to the first coprecipitate, stirred under the same conditions for about 40 minutes, then transferred to a pyrex tray, and dried at 120° C. for 24 hours.

The dried sample was ground by a grinder, and only particles having a size of 355 μm or less were collected using a standard sieve, and the powder was kneaded while spraying a mixed solution of isopropyl alcohol:distilled water in a weight ratio of 1:1.

The kneaded powder was extruded into cylindrical pellets (diameter=0.6 cm). The molded pellets were dried, and then finally heat-treated at 470° C. while flowing air to produce a catalyst.

Comparative Example 1 (Corresponding to Sample 2)

Precursor aqueous solution A: 0.2 g of $KNO_3$, 11.7 g of $CsNO_3$, 63.4 g of $Fe(NO_3)_3 \cdot 9H_2O$ and 281.2 g of $Co(NO_3)_2 \cdot 6H_2O$ were sequentially charged into a beaker containing 183 g of distilled water, and then dissolved with stirring.

Precursor aqueous solution B: 58.6 g of $Bi(NO_3)_3 \cdot 5H_2O$ was added to a beaker containing 56 g of distilled water, and 17.6 g of nitric acid was added with stirring.

Precursor solution C: 255.9 g of $(NH_4)_6Mo_7O_{24} \cdot 4H_2O$ was added to a beaker containing 1020 g of distilled water and dissolved with stirring.

The precursor aqueous solutions A and B were mixed and stirred for 1 hour, then added to the precursor aqueous solution C (40° C.) under stirring using a dropping funnel and allowed to precipitate. Dropping was carried out for 2 hour. After completion of the dropping, the precipitate was stirred under the same conditions for 1 hour.

The coprecipitate subjected to aging was transferred to a pyrex tray, and dried at 120° C. for 24 hours.

The dried sample was ground by a grinder, and only particles having a size of 355 μm or less were collected using a standard sieve, and the powder was kneaded while spraying a mixed solution of isopropyl alcohol:distilled water in a weight ratio of 1:1.

The kneaded powder was extruded into cylindrical pellets (diameter=0.6 cm). The molded pellets were dried, and then finally heat-treated at 470° C. while flowing air to produce a catalyst.

Example 2 (Sample 3)

Precursor aqueous solution A: 0.2 g of $KNO_3$, 11.7 g of $CsNO_3$, 63.4 g of $Fe(NO_3)_3 \cdot 9H_2O$ and 281.2 g of Co(NO$_3$)$_2$·6H$_2$O were sequentially charged into a beaker containing 183 g of distilled water, and then dissolved with stirring.

Precursor aqueous solution B: 29.3 g of Bi(NO$_3$)$_3$·5H$_2$O was added to a beaker containing 100 g of distilled water, and 14 g of nitric acid was added with stirring.

Precursor solution C: 245.2 g of (NH$_4$)$_6$Mo$_7$O$_{24}$·4H$_2$O was added to a beaker containing 900 g of distilled water, and dissolved with stirring.

Precursor aqueous solution C': 5.4 g of (NH$_4$)$_6$Mo$_7$O$_{24}$·4H$_2$O was added to a beaker containing 180 g of distilled water, and dissolved with stirring.

The precursor aqueous solution A was added to the precursor aqueous solution C (40° C.) under stirring using a dropping funnel and allowed to precipitate (first coprecipitate). Dropping was carried out for about 1 hour, and then the precipitate was stirred under the same conditions for about 30 minutes.

At the same time, the precursor aqueous solution B was added to the precursor aqueous solution C' (40° C.) under stirring using a dropping funnel (second coprecipitate). Dropping was carried out for about 30 minutes and then the precipitate was stirred under the same conditions for about 1 hour.

The second coprecipitate was subjected to aging and was added to the first coprecipitate, stirred under the same conditions for about 40 minutes, then transferred to a pyrex tray, and dried at 120° C. for 24 hours.

The dried sample was ground by a grinder, and only particles having a size of 355 μm or less were collected using a standard sieve, and the powder was kneaded while spraying a mixed solution of isopropyl alcohol:distilled water in a weight ratio of 1:1.

The kneaded powder was extruded into cylindrical pellets (diameter=0.6 cm). The molded pellets were dried, and then finally heat-treated at 470° C. while flowing air to produce a catalyst.

Example 3 (Sample 4)

Precursor aqueous solution A: 0.2 g of KNO$_3$, 11.7 g of CsNO$_3$, 63.4 g of Fe(NO$_3$)$_3$·9H$_2$O and 281.2 g of Co(NO$_3$)$_2$·6H$_2$O were sequentially charged into a beaker containing 183 g of distilled water, and then dissolved with stirring.

Precursor aqueous solution B: 70.3 g of Bi(NO$_3$)$_3$·5H$_2$O was added to a beaker containing 100 g of distilled water, and 14 g of nitric acid was added with stirring.

Precursor solution C: 245.2 g of (NH$_4$)$_6$Mo$_7$O$_{24}$·4H$_2$O was added to a beaker containing 900 g of distilled water, and dissolved with stirring.

Precursor aqueous solution C': 12.8 g of (NH$_4$)$_6$Mo$_7$O$_{24}$·4H$_2$O was added to a beaker containing 180 g of distilled water, and dissolved with stirring.

The precursor aqueous solution A was added to the precursor aqueous solution C (40° C.) under stirring using a dropping funnel and allowed to precipitate. Dropping was carried out for about 1 hour, and then the precipitate was stirred under the same conditions for about 30 minutes (first coprecipitate).

At the same time, the precursor aqueous solution B was added to the precursor aqueous solution C' (40° C.) under stirring using a dropping funnel (second coprecipitate). Dropping was carried out for about 30 minutes, and then the precipitate was stirred under the same conditions for about 1 hour.

The second coprecipitate was subjected to aging and was added to the first coprecipitate, stirred under the same conditions for about 40 minutes, then transferred to a pyrex tray, and dried at 120° C. for 24 hours.

The dried sample was ground by a grinder, and then only particles having a size of 355 μm or less were collected using a standard sieve, and the powder was kneaded while spraying a mixed solution of isopropyl alcohol:distilled water in a weight ratio of 1:1.

The kneaded powder was extruded into cylindrical pellets (diameter=0.6 cm). The molded pellets were dried, and then finally heat-treated at 470° C. while flowing air to produce a catalyst.

Example 4 (Sample 5)

Precursor aqueous solution A: 0.2 g of KNO$_3$, 11.7 g of CsNO$_3$, 63.4 g of Fe(NO$_3$)$_3$·9H$_2$O and 281.2 g of Co(NO$_3$)$_2$·6H$_2$O were sequentially charged into a beaker containing 183 g of distilled water, and then dissolved with stirring.

Precursor aqueous solution B: 82 g of Bi(NO$_3$)$_3$·5H$_2$O was added to a beaker containing 100 g of distilled water, and 14 g of nitric acid was added with stirring.

Precursor solution C: 245.2 g of (NH$_4$)$_6$Mo$_7$O$_{24}$·4H$_2$O was added to a beaker containing 900 g of distilled water, and dissolved with stirring.

Precursor aqueous solution C': 14.5 g of (NH$_4$)$_6$Mo$_7$O$_{24}$·4H$_2$O was added to a beaker containing 180 g of distilled water, and dissolved with stirring.

The precursor aqueous solution A was added to the precursor aqueous solution C (40° C.) under stirring using a dropping funnel and allowed to precipitate (first coprecipitate). Dropping was carried out for about 1 hour, and then the precipitate was stirred under the same conditions for about 30 minutes.

At the same time, the precursor aqueous solution B was added to the precursor aqueous solution C' (40° C.) under stirring using a dropping funnel (second coprecipitate). Dropping was carried out for about 30 minutes, and then the precipitate was stirred under the same conditions for about 1 hour.

The second coprecipitate was subjected to aging and was added to the first coprecipitate, stirred under the same conditions for about 40 minutes, then transferred to a pyrex tray, and dried at 120° C. for 24 hours.

The dried sample was ground by a grinder, and then only particles having a size of 355 μm or less were collected using a standard sieve, and the powder was kneaded while spraying a mixed solution of isopropyl alcohol:distilled water in a weight ratio of 1:1.

The kneaded powder was extruded into cylindrical pellets (diameter=0.6 cm). The molded pellets were dried, and then finally heat-treated at 470° C. while flowing air to produce a catalyst.

Example 5 (Corresponding to Sample 6)

Precursor aqueous solution A: 0.2 g of KNO$_3$, 11.7 g of CsNO$_3$, 73.2 g of Fe(NO$_3$)$_3$·9H$_2$O and 281.2 g of Co(NO$_3$)$_2$·6H$_2$O were sequentially charged into a beaker containing 183 g of distilled water, and then dissolved with stirring.

Precursor aqueous solution B: 58.6 g of Bi(NO$_3$)$_3$·5H$_2$O was added to a beaker containing 100 g of distilled water, and 14 g of nitric acid was added with stirring.

Precursor solution C: 245.2 g of (NH$_4$)$_6$Mo$_7$O$_{24}$·4H$_2$O was added to a beaker containing 900 g of distilled water and dissolved with stirring.

Precursor aqueous solution C': 10.7 g of $(NH_4)_6Mo_7O_{24} \cdot 4H_2O$ was added to a beaker containing 180 g of distilled water and dissolved with stirring.

The precursor aqueous solution A was added to the precursor aqueous solution C (40° C.) under stirring using a dropping funnel and allowed to precipitate (first coprecipitate). Dropping was carried out for about 1 hour, and then the precipitate was stirred under the same conditions for about 30 minutes.

At the same time, the precursor aqueous solution B was added to the precursor aqueous solution C' (40° C.) under stirring using a dropping funnel (second coprecipitate). Dropping was carried out for about 30 minutes, and then the precipitate was stirred under the same conditions for about 1 hour.

The second coprecipitate was subjected to aging and was added to the first coprecipitate, further stirred under the same conditions for about 40 minutes, then transferred to a pyrex tray, and dried at 120° C. for 24 hours.

The dried sample was ground by a grinder, and then only particles having a size of 355 μm or less were collected using a standard sieve, and the powder was kneaded while spraying a mixed solution of isopropyl alcohol:distilled water in a weight ratio of 1:1.

The kneaded powder was extruded into cylindrical pellets (diameter=0.6 cm). The molded pellets were dried, and then finally heat-treated at 470° C. while flowing air to produce a catalyst.

Example 6 (Corresponding to Sample 7)

Precursor aqueous solution A: 63.4 g of $Fe(NO_3)_3 \cdot 9H_2O$ and 281.2 g of $Co(NO_3)_2 \cdot 6H_2O$ were sequentially charged into a beaker containing 183 g of distilled water, and then dissolved with stirring.

Precursor aqueous solution B: 0.2 g of $KNO_3$, 11.7 g of $CsNO_3$, and 58.6 g of $Bi(NO_3)_3 \cdot 5H_2O$ were added to a beaker containing 100 g of distilled water, and 14 g of nitric acid was added with stirring.

Precursor solution C: 245.2 g of $(NH_4)_6Mo_7O_{24} \cdot 4H_2O$ was added to a beaker containing 900 g of distilled water, and dissolved with stirring.

Precursor aqueous solution C': 10.7 g of $(NH_4)_6Mo_7O_{24} \cdot 4H_2O$ was added to a beaker containing 180 g of distilled water, and dissolved with stirring.

The precursor aqueous solution A was added to the precursor aqueous solution C (40° C.) under stirring using a dropping funnel and allowed to precipitate (first coprecipitate). Dropping was carried out for about 1 hour, and then the precipitate was stirred under the same conditions for about 30 minutes.

At the same time, the precursor aqueous solution B was added to the precursor aqueous solution C' (40° C.) under stirring using a dropping funnel (second coprecipitate). Dropping was carried out for about 30 minutes, and then the precipitate was stirred under the same conditions for about 1 hour.

The second coprecipitate was subjected to aging and was added to the first coprecipitate, further stirred under the same conditions for about 40 minutes, then transferred to a pyrex tray, and dried at 120° C. for 24 hours.

The dried sample was ground by a grinder, and then only particles having a size of 355 μm or less were collected using a standard sieve, and the powder was kneaded while spraying a mixed solution of isopropyl alcohol:distilled water in a weight ratio of 1:1.

The kneaded powder was extruded into cylindrical pellets (diameter=0.6 cm). The molded pellets were dried, and then finally heat-treated at 470° C. while flowing air to produce a catalyst.

Example 7 (corresponding to Sample 8)

Precursor aqueous solution A: 63.4 g of $Fe(NO_3)_3 \cdot 9H_2O$ and 281.2 g of $Co(NO_3)_2 \cdot 6H_2O$ were sequentially charged into a beaker containing 183 g of distilled water, and then dissolved with stirring.

Precursor aqueous solution B: 0.2 g of $KNO_3$, 11.7 g of $CsNO_3$, and 58.6 g of $Bi(NO_3)_3 \cdot 5H_2O$ were added to a beaker containing 100 g of distilled water, and 14 g of nitric acid was added with stirring.

Precursor solution C: 245.2 g of $(NH_4)_6Mo_7O_{24} \cdot 4H_2O$ was added to a beaker containing 900 g of distilled water, and dissolved with stirring.

Precursor aqueous solution C': 10.7 g of $(NH_4)_6Mo_7O_{24} \cdot 4H_2O$ was added to a beaker containing 180 g of distilled water, and dissolved with stirring.

The precursor aqueous solution A was added to the precursor aqueous solution C (40° C.) under stirring using a dropping funnel and allowed to precipitate (first coprecipitate). Dropping was carried out for about 1 hour, and then the precipitate was stirred under the same conditions for about 30 minutes.

At the same time, the precursor aqueous solution B was added to the precursor aqueous solution C' (40° C.) under stirring using a dropping funnel (second coprecipitate). Dropping was carried out for about 30 minutes, and then the precipitate was stirred under the same conditions for about 1 hour.

The second coprecipitate was subjected to aging and was added to the first coprecipitate, further stirred under the same conditions for about 40 minutes, then transferred to a pyrex tray, and dried at 120° C. for 24 hours.

The dried sample was ground by a grinder, and then only particles having a size of 355 μm or less were collected using a standard sieve, and the powder was kneaded while spraying a mixed solution of isopropyl alcohol:distilled water in a weight ratio of 1:1.

The kneaded powder was extruded into cylindrical pellets (diameter=0.6 cm). The molded pellets were dried, and then finally heat-treated at 450° C. while flowing air to produce a catalyst.

XRD Measurement

Figure 1:
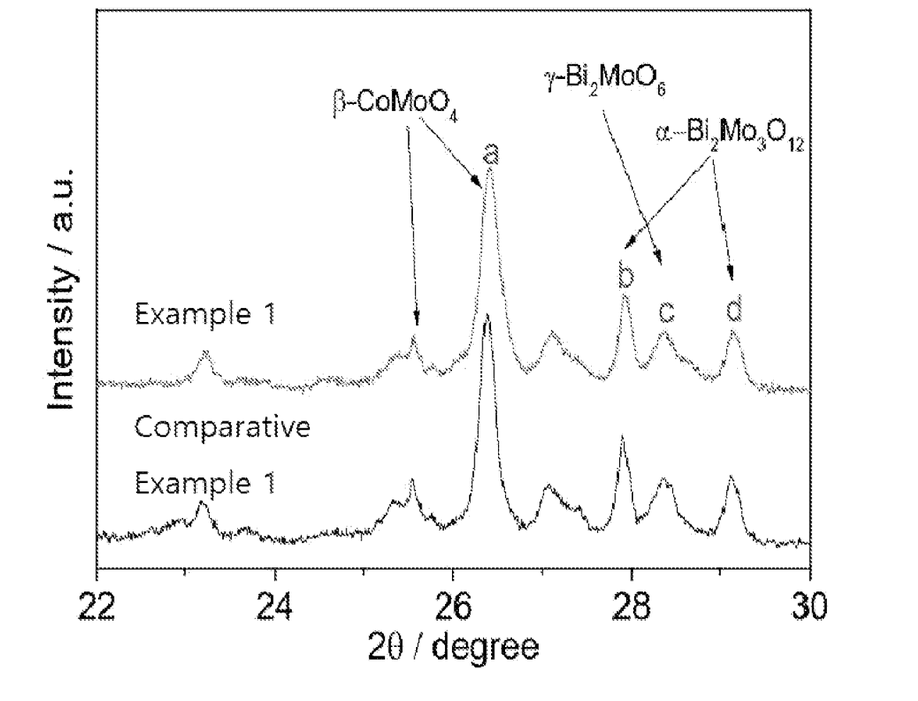
FIG. 1 is an X-ray diffraction (XRD) image of a catalyst according to Example 1 of the present invention and Comparative Example 1.

FIG. 1 is an X-ray diffraction (XRD) image of a catalyst according to Example 1 of the present invention and Comparative Example 1.

Referring to FIG. 1, in the catalyst produced according to Example 1 of the present invention, the cobalt-molybdenum-oxygen crystal structure, the bismuth-molybdenum-oxygen crystal structure, and the peak according to each structure can be clearly confirmed. In particular, it can be clearly seen that in Example 1 of the present invention, the diffraction peak corresponding to β-$CoMoO_4$ (a) is relatively broad. This means that the β-$CoMoO_4$ phase is highly dispersed.

Measurement of Element Content

The surface composition and total composition of the catalysts according to Example 1 and Comparative Example 1 were measured for each element.

The surface composition was measured using XPS and the total composition was measured using ICP-OES.

The measured compositions are summarized in Table 1 below.

TABLE 1

| Remarks | Surface (Atomic %) | | | Total (Atomic %) | | |
|---|---|---|---|---|---|---|
| | Bi | Co | Mo | Bi | Co | Mo |
| Example 1 | 1.8 | 1.3 | 20.2 | 1.0 | 8.1 | 12.5 |
| Comparative Example 1 | 1.0 | 1.4 | 22.0 | 1.0 | 8.2 | 12.6 |

Referring to Table 1, it can be clearly confirmed that the catalyst according to Example of the present invention contains a relatively large amount of bismuth on the surface and contains a relatively large amount of cobalt in the core, in particular, the value represented by the following Calculation Formula 1 is about 11.2.

BARS/BART>6         [Calculation Formula 1]

in Calculation Formula 1,

BARS is the molar content (atomic ratio, %) of bismuth/the molar content (atomic ratio, %) of cobalt on the catalyst surface, measured by XPS, and BART is the molar content (atomic ratio, %) of bismuth/the molar content (atomic ratio, %) of cobalt in the entire catalyst, measured by ICP-OES.

Oxidative Dehydrogenation of Butene

The oxidative dehydrogenation of butene was carried out using the catalysts produced in Examples and Comparative Examples above.

The reactor had an inner diameter of ¾ inch and a length of 55 cm, and the reaction was carried out in a tube reactor in which the temperature was controlled by the molten salt. At this time, the temperature of the molten salt was 320° C.

The inside of the reactor was filled with an inert alumina ball, a catalyst and an inert alumina ball by 28cc, 20cc and 59 cc in this order.

The gas hourly space velocity (GHSV) was 100 h$^{-1}$ based on 1-butene.

The product was analyzed using a gas chromatograph (GC) equipped with a thermal conductivity detector (TCD) and a flame ionization detector (FID).

The experimental results are shown in Table 2 below.

Examples, and they are also generally excellent in $CO_x$ selectivity as compared with Comparative Examples.

The invention claimed is:

1. A method for producing a catalyst for oxidative dehydrogenation of butene comprising:

producing a first coprecipitate by mixing a first aqueous solution containing a cobalt salt, a salt of at least one of Fe, Mn and Cu, a salt of at least one of K and Cs, and a salt of cobalt with a second aqueous solution containing ammonium molybdate, and performing co-precipitation while stirring at 30° C. to 50° C. for 0.5 to 2 hours;

producing a second coprecipitate by mixing a third aqueous solution of bismuth (Bi) with a fourth aqueous solution containing ammonium molybdate, and performing co-precipitation while stirring at 30° C. to 50° C. for 0.5 to 2 hours; and aging the second coprecipitate; and mixing the first coprecipitate and the second coprecipitate to form a slurry;

drying the slurry;

grinding and calcining the dried slurry to produce catalyst particles, wherein a surface composition of the catalyst particles, measured by X-ray photoelectron spectroscopy (XPS), has a molar content of bismuth (Bi) that is higher than a molar content of cobalt (Co), a composition according to Composition Formula 1;

$Mo_aBi_bCo_c(M1)_d(M4)_eO_f$     [Composition Formula 1]

in Composition Formula 1, Mo is molybdenum, Bi is bismuth, Co is cobalt, O is oxygen, M1 is one or more of potassium (K) and cesium (Cs), M4 is one or more of iron (Fe), manganese (Mn), and copper (Cu), a is from 9 to 25, b is from 0.5 to 2, c is from 1 to 10, d is from 0.01 to 1, e is from 0.5 to 5, and f is from 30 to 50, wherein the catalyst satisfies the following Calculation Formula 1

BARS/BART>6,         [Calculation Formula 1]

in Calculation Formula 1

BARS is the molar content of bismuth/the molar content of cobalt on the catalyst surface, measured by XPS, and

TABLE 2

| | Catalyst | Butene:oxygen:nitrogen:steam (volume ratio) | Pressure (psi) | Conversion rate (mol %) | Butadiene selectivity(mol %) | $CO_x$ Selectivity (mol %) |
|---|---|---|---|---|---|---|
| Example 1-1 | Example 1 | 1:1:12:4 | 12 | 96.5 | 94.6 | 2.31 |
| Example 1-2 | Example 1 | 1:1:10:3 | 0 | 96.9 | 96.0 | 1.20 |
| Comparative Example 1-1 | Comparative Example 1 | 1:1:10:3 | 0 | 85.5 | 95.4 | 1.18 |
| Example 2-1 | Example 2 | 1:1:12:4 | 0 | 77.8 | 95.6 | 0.69 |
| Example 3-1 | Example 3 | 1:1:12:4 | 0 | 92.8 | 96.1 | 0.88 |
| Example 4-1 | Example 4 | 1:1:12:4 | 0 | 92.2 | 96.5 | 0.72 |
| Example 5-1 | Example 5 | 1:1:12:4 | 12 | 96.8 | 94.6 | 2.14 |
| Example 6-1 | Example 6 | 1:1:12:4 | 12 | 97.1 | 94.7 | 2.14 |
| Example 7-1 | Example 7 | 1:1:12:4 | 12 | 97.8 | 94.3 | 2.69 |

Referring to Table 2 above, it can be confirmed that the catalysts produced according to Examples of the present invention exhibit an excellent effect of about 10% points or more in conversion rate as compared with Comparative BART is a molar content of bismuth/a molar content of cobalt in the entire catalyst, measured by inductively coupled plasma optical emission spectroscopy (ICP-OES).

2. The method for producing a catalyst for oxidative dehydrogenation of butene according to claim 1, further comprising classifying the catalyst particles after the grinding.

3. The method for producing a catalyst for oxidative dehydrogenation of butene according to claim 2, wherein as part of the classifying, only particles having a size of 355 μm or less are collected.

* * * * *